United States Patent
Webb et al.

(10) Patent No.: US 8,873,060 B2
(45) Date of Patent: Oct. 28, 2014

(54) WATER-IN-FUEL SENSOR

(75) Inventors: David John Webb, Shrewsbury (GB); Chi Zhang, ShenZhen (CN)

(73) Assignee: Aston University, Birmingham (GB)

( * ) Notice: Subject to any disclaimer, the term of this patent is extended or adjusted under 35 U.S.C. 154(b) by 295 days.

(21) Appl. No.: 13/393,946

(22) PCT Filed: Aug. 27, 2010

(86) PCT No.: PCT/GB2010/001623
§ 371 (c)(1),
(2), (4) Date: Mar. 2, 2012

(87) PCT Pub. No.: WO2011/027099
PCT Pub. Date: Mar. 10, 2011

(65) Prior Publication Data
US 2012/0162654 A1 Jun. 28, 2012

(30) Foreign Application Priority Data
Sep. 4, 2009 (GB) .................... 0915492.3

(51) Int. Cl.
| | |
|---|---|
| G01N 21/00 | (2006.01) |
| G01N 21/55 | (2014.01) |
| G02B 6/00 | (2006.01) |
| G01J 1/04 | (2006.01) |
| G01J 1/42 | (2006.01) |
| G01J 5/08 | (2006.01) |
| G01N 21/84 | (2006.01) |
| G01N 21/41 | (2006.01) |
| G01N 33/28 | (2006.01) |
| G01N 21/43 | (2006.01) |

(52) U.S. Cl.
CPC ............... *G01N 21/41* (2013.01); *G01N 21/84* (2013.01); *G01N 21/431* (2013.01); *G01N 33/2847* (2013.01)

USPC ......... 356/436; 356/445; 385/12; 250/227.14

(58) Field of Classification Search
None
See application file for complete search history.

(56) References Cited

U.S. PATENT DOCUMENTS

| | | | |
|---|---|---|---|
| 5,005,005 A | 4/1991 | Brossia et al. | |
| 2005/0105841 A1 | 5/2005 | Luo et al. | |

(Continued)

FOREIGN PATENT DOCUMENTS

| | | |
|---|---|---|
| JP | 62-168034 | 7/1987 |
| JP | 63-092241 | 4/1988 |

(Continued)

OTHER PUBLICATIONS

Yu, Jian-ming, "Photosensitive polymer optical fibers and gratings," abstract. 2005.*

(Continued)

*Primary Examiner* — Gordon J Stock, Jr.
(74) *Attorney, Agent, or Firm* — Calfee, Halter & Griswold LLP

(57) ABSTRACT

An uncoated polymer optical fiber (POF) that is sensitive to a chemical (e.g. water) and is used to generate a detectable change in its optical properties for the purpose of detecting that chemical when it is dissolved in liquid fuel. The presence of the chemical directly affects the optical properties of the optical fiber. The POF may be made of water-permeable plastic material and may have a grating section comprising a periodic refractive index modulation that exhibits a characteristic reflection or transmission profile to be monitored by a detector. The water-permeability of the constituent material of the POF permits diffusion of water into the fiber, thereby affecting its refractive index or geometry and hence altering the characteristic reflection or transmission profile of the grating section.

18 Claims, 1 Drawing Sheet

(56) References Cited

U.S. PATENT DOCUMENTS

| | | | |
|---|---|---|---|
| 2007/0116402 A1 | 5/2007 | Slade et al. | |
| 2008/0013879 A1 | 1/2008 | Mossman | |
| 2008/0043242 A1* | 2/2008 | Emmerson et al. | 356/477 |
| 2009/0034901 A1 | 2/2009 | Takabayashi et al. | |
| 2009/0059209 A1* | 3/2009 | Nguyen et al. | 356/73.1 |
| 2010/0290062 A1 | 11/2010 | Phan Huy et al. | |

FOREIGN PATENT DOCUMENTS

| | | |
|---|---|---|
| JP | 2001-013334 | 1/2001 |
| JP | 2001-516011 | 9/2001 |
| JP | 2007-071863 | 3/2007 |
| JP | 2007-214430 | 8/2007 |
| WO | 2006/126468 | 11/2006 |

OTHER PUBLICATIONS

UKIPO Search Report for related case, GB 0915492.3, Nov. 2009.
S. D. Puckett, G. E. Pacey: "Detection of water in jet fuel using layer-by-layer thin film coated long period grating sensor". Talanta 78 (2009) 300-304.
D. Sáez-Rodriguez, J. L. Cruz Munoz, I. Johnson, D. J. Webb, M. C. J. Large, A. Argyros: "Long period fibre gratings photoinscribed in a microstructured polymer optical fibre by UV radiation". Proc. of SPIE vol. 7357, 73570L (2009).
T. L. Yeo, T. Sun, K. T. V. Grattan: "Fibre-optic sensor Technologies for humidity and moisture measurement". Sensors and Actuators A 144 (2008) 280-295.
S. Muto, O. Suzuki, T. Amano, M. Morisawa: "A plastic optical fibre sensor for real-time humidity monitoring". Meas. Sci. Technol. 14 (2003) 746-750.
N. G. Harbach: "Fiber bragg gratings in polymer optical fibers", Thèse EPFL, No. 4021 (2008).
S. W. James, R. P. Tatam: "Optical fibre long-period grating sensors: characteristics and application" Meas. Sci. Technol. 14 (2003) R49-R61.
I. Johnson, D. Webb: "Polymer-fiber grating sensors", SPIE Newsroom, May 4, 2010.
English translation of Office Action dated Jul. 30, 2013, for corresponding Japanese Patent Application No. 2012-527376.
Notice of Grant dated Jun. 3, 2014, for Japanese Patent Application No. 2012-527376.

* cited by examiner

WATER-IN-FUEL SENSOR

CROSS REFERENCE TO RELATED APPLICATIONS

The present application is a national phase entry under 35 U.S.C. §371 and claims priority to International Application No. PCT/GB2010/001623 filed on Aug. 27, 2010, for WATER-IN-FUEL SENSOR and also claims the benefit of Great Britain Patent Application No. 0915492.3 filed on Sep. 4, 2009, the entire disclosures all of which are fully incorporated herein by reference.

FIELD OF THE INVENTION

The invention relates to a sensor for detecting the amount of an additive dissolved in liquid fuel. For example, the invention may be used in a device for detecting the presence of water in aviation fuel (kerosene).

BACKGROUND TO THE INVENTION

In general, liquid fuels produced from petroleum (e.g. gasoline, diesel, kerosene) have chemical additives dissolved therein to enhance certain properties (e.g. to facilitate handling or to improve performance). The proportion of such additives may be very small (e.g. less than 100 ppm) yet may need to be controlled carefully to ensure the fuel exhibits the desired properties.

Water is not usually used as an additive, but is normally present in small amounts in liquid fuel. Water can exist in the fuel in three states: dissolved in the fuel, in a separate liquid phase (known as free water), or in a fuel-water emulsion. The existence of free water or a fuel-water emulsion in use can cause problems, particularly in aerospace applications where the chance of the water freezing is increased. It is desirable to monitor the amount of water dissolved in fuel, e.g. a measure of how close the fuel is to saturation, to provide an indication of the risk of free water or a fuel-water emulsion occurring.

Water-in-fuel sensors for detecting undissolved water have previously been proposed. For example, U.S. Pat. No. 4,638,305 describes apparatus for detecting free water in fuel by sensing its resistive properties. Similarly, U.S. Pat. No. 5,642,098 describes detecting water in an oil-water emulsion by monitoring the dielectric properties of the emulsion. Optical techniques have also been proposed. For example, U.S. Pat. No. 5,121,986 describes immersing a plurality of optical guides into fuel, each guide having a different refractive index such that the water content could be sensed by comparing or correlating changes in the intensity of light propagating through the guides.

More recently, a technique of detecting water dissolved in kerosene using a water-sensitive coating on a silica-based optical fibre containing a long period grating (LPG) has been demonstrated [1]. Here the presence of water causes a variation in the refractive index of the coating, whereby the LPG optical fibre operates as a spectral loss element. The central wavelength of the attenuation band in a transmitted spectrum is monitored to detect the amount of water dissolved in the fuel.

SUMMARY OF THE INVENTION

At its most general, the invention proposes manufacturing an optical fibre from material that is sensitive to a chemical as a means of generating a detectable change in optical properties of the optical fibre to detect that chemical when dissolved in liquid fuel. In other words the presence of the chemical directly affects the optical properties of the optical fibre in a unique manner. This may be distinguished from conventional sensors in which changes in an intermediate material are detected using an optical fibre.

In a particular aspect of interest, the invention may provide a polymer optical fibre made of water-permeable material that is adapted to sense water in liquid fuel.

According to this aspect, there may be provided a water-in-fuel sensor comprising: a probe for immersing in fuel, the probe comprising an uncoated polymer optical fibre (POF) for guiding optical radiation, the POF being made of water-permeable plastic material and having a grating section comprising a periodic refractive index modulation that exhibits a characteristic reflection or transmission profile; a light source optically coupled to the probe to deliver optical radiation into the POF; and a detector arranged to receive optical radiation reflected from or transmitted by the grating section and monitor the characteristic reflection or transmission profile of the grating section. In use, the uncoated polymer optical fibre is exposed directly to the fuel. The water-permeability of the constituent material of the POF permits diffusion of water into the fibre, thereby affecting its refractive index or geometry and hence altering the characteristic reflection or transmission profile of the grating section. For example, the diffused water may cause the fibre to alter in size, e.g. swell, which in turn alters its optical characteristics.

Herein, "fuel" may mean liquid fuel produced from petroleum, e.g. gasoline, diesel and kerosene. "Water-permeable plastic material" means a polymeric material into which water can diffuse. The rate of water diffusion into the material is a factor affecting the response time of the device, so materials in which the diffusion rate is high may be preferred.

The POF may be made of a poly(methyl methacrylate)-based (PMMA-based) material. For example, the POF may have a cladding made of substantially pure PMMA surrounding a core made of PMMA mixed with one or more other polymers to increase its refractive index. The other polymers in the core may include one or more photosensitivity enhancing polymers, to improve the inscription of the grating section. The POF is preferably a single mode fibre, to facilitate accurate detection.

The detection of the sensitivity of PMMA-based optical fibres to water is already known, as is the means for monitoring this sensitivity using a LPG formed in the fibre [2]. However, this arrangement was based on fibres immersed in water, whereas the present invention is concerned with monitoring the very small amounts (e.g. less than 100 ppm, preferably less than 10 ppm) of water dissolved in fuel. Indeed, the use of gratings in optical fibres as a means of measuring humidity is well known [3], as is the particular use of plastic optical fibres in the same field [4, 5]. However, these prior arrangement do not extend to the detection of small quantities of water present in another medium.

To guide optical radiation, the POF may comprise a core made from water-permeable plastic having a first refractive index, and cladding surrounding the core having a second refractive index, the second refractive index being lower than the first refractive index. The periodic refractive index modulation may be confined within the core or exist throughout the fibre.

The periodic refractive index modulation may be produced by mechanical deformation coupled with heating, or by direct photoinscription e.g. using UV light.

The cladding may be lapped or otherwise thinned at the grating section. This feature has the advantage of bringing the core closer to the fuel, thereby decreasing the time it takes for water to diffuse to the grating section and hence improving the sensor response time. The POF may have a diameter of 250 µm or less. Smaller diameters may be preferred because this improves the sensor's response time.

The grating section may comprise a Bragg grating (FBG) (e.g. short period grating, where the period of the refractive index modulation is of the order of a peak reflected wavelength, or "Bragg wavelength") or a long period grating (LPG), where the period of the refractive index modulation is an order of magnitude or more greater, e.g. 100 µm or more. The diffusion of the water into the fibre may affect both the refractive index and the grating spacing due to swelling of the fibre. The grating section is used to provide a measurable interaction between input optical radiation and the fibre properties. In particular, the resonant wavelength of a grating structure depends on the refractive index of the medium in which the grating is formed and the period of the grating. The resonant wavelength may be an aspect of characteristic reflection profile (e.g. of an FBG) or the characteristic transmission profile (e.g. of an LPG) used to monitor the water content of the fibre.

The detector may be arranged to monitor the Bragg wavelength of the FBG or LPG. This may be done in any conventional manner. For example, the light source may be arranged to interrogate the probe with a broadband signal (i.e. a signal having a wide range of wavelengths) and the detector may be arranged to analyse the spectrum reflected by the grating section. Other approaches may include using a tuneable laser or edge filter. For example, the light source may be arranged to couple optical radiation with a single tuneable frequency into the POF, and the detector may be arranged in a feedback loop with the light source to detect a resonant frequency of the grating section. Alternatively, the edge filter may be optically coupled to receive light reflected or transmitted by the grating section. The edge filter has a transmission that varies with wavelength, so the resonant wavelength may be deduced by monitoring the amount of power transmitted through the edge filter.

The sensor proposed herein provides an electrically passive approach that may enable real-time monitoring of small quantities (e.g. 1-100 ppm) of water dissolved in fuel, especially aviation fuel.

Although expressed in terms of the particular aspect of interest, the present invention may also provide sensors for other types of chemical in solution, the only requirement being to find a material that is both permeable to that chemical and can be formed as an optical fibre with periodic refractive index modulations.

BRIEF DESCRIPTION OF THE DRAWINGS

An embodiment of the invention is described in detail below with reference to the accompanying drawings, in which.

DETAILED DESCRIPTION; FURTHER OPTIONS AND PREFERENCES

Figure 1:
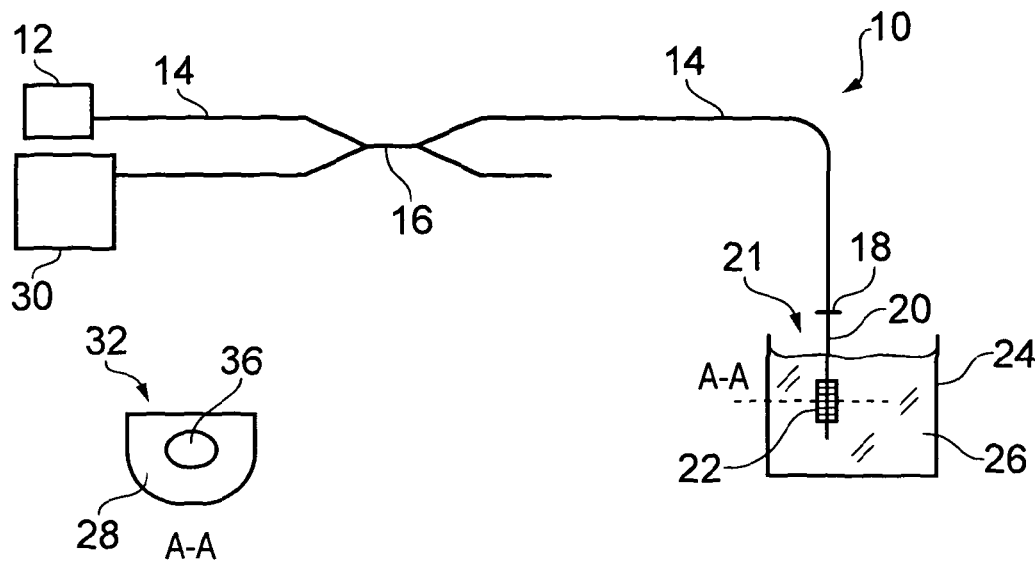
FIG. 1 is a schematic diagram showing a water-in-fuel sensor that is an embodiment of the invention.

FIG. 1 shows an embodiment of a water-in-fuel sensor 10. The sensor comprises a light source 12, e.g. a broadband white light source such as halogen lamp or the like, optically coupled to a probe 21 via an optical fibre 14. In this embodiment, the optical fibre 14 is a conventional silica-based fibre, but any other means of conveying the output of the light source 12 to the probe 21 may be used.

The probe comprises a length of PMMA-based fibre 20 that is coupled to the optical fibre 14 at connector 18 in a conventional manner. The PMMA-based fibre 20 may have a conventional step-index design, comprising a core having a circular cross-section held within a circular cladding. The cladding may be pure PMMA, whilst the core may include additives mixed with the PMMA to increase its refractive index. Alternatively, the fibre may have a gradient index profile or possess a microstructured geometry in which light guiding is enabled by a suitable pattern of holes running along the fibre length.

The probe includes a grating section 22, in which the cladding is uncoated and a periodic refractive index modulation is formed in the core. In this embodiment, the periodic refractive index modulation is a fibre Bragg grating (FBG) having a period selected to reflect light having a wavelength of around 1565 nm.

As shown in the cross-section inset in FIG. 1, the uncoated cladding 28 is lapped 32 in the grating section 22 to bring the core 36 into closer proximity with the outer surface of the fibre 20 and hence improve the sensor's response time.

The grating section 22 of the probe 21 is immersed in fuel 26 (e.g. kerosene) held in a container 24 (e.g. fuel tank or the like).

In use, the white light emitted by the light source 12 is coupled to the probe 21. The grating section transmits most wavelengths, which will be emitted from the end of the probe into the fuel, but reflects a small range of wavelengths in accordance with a characteristic reflection profile, which depends on the period of the grating and the refractive index of the fibre. As demonstrated below, diffusion of water into the fibre 20 at the grating section 22 causes a change in the fibre properties, which manifests as a change in the characteristic reflection profile.

Optical radiation reflected from the probe 21 travels back towards the light source through optical fibre 14. To detect the reflected light, a coupler 16 is inserted into the optical fibre 14, which acts to transfer the reflected light (but not the forward directing white light) into a detector 30. In this embodiment, the detector 30 is an optical spectrum analyser arranged to monitor the peak (largest amplitude) reflected wavelength (the Bragg wavelength).

Figure 2:
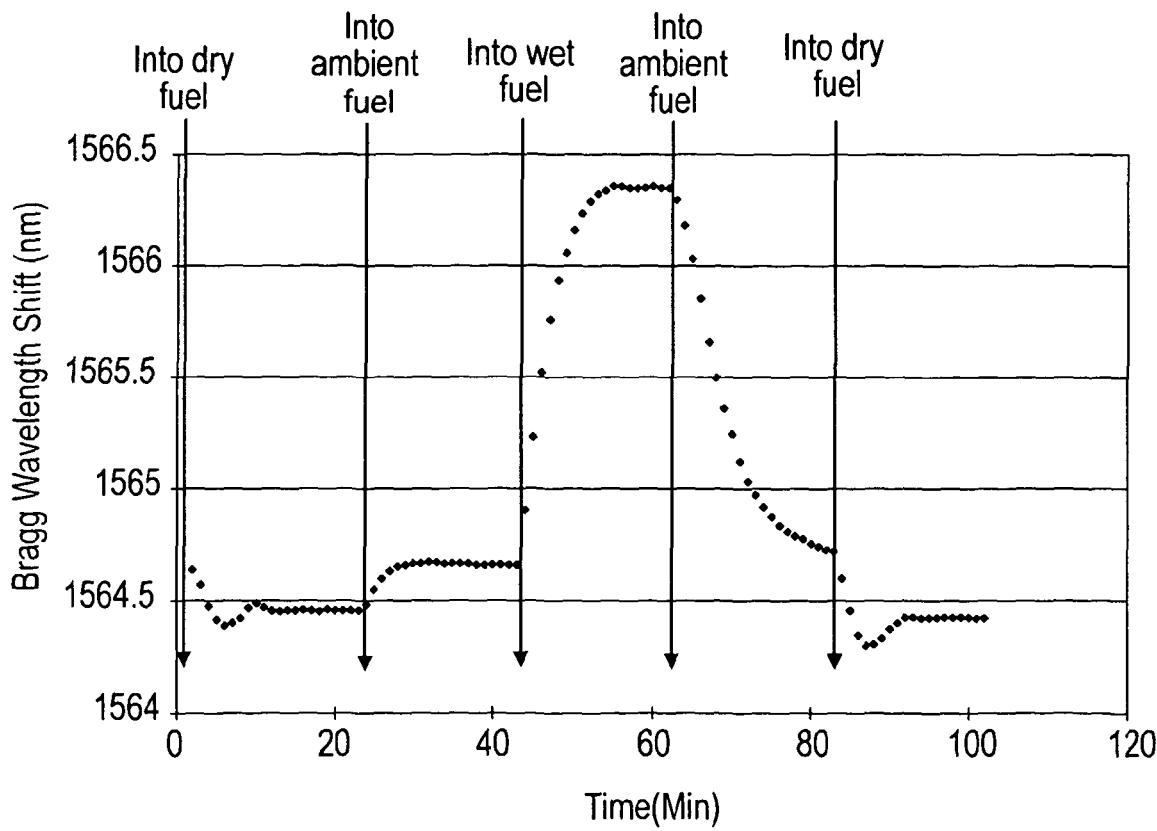
FIG. 2 is a graph depicting Bragg wavelength shift with time as a probe is inserted into dry fuel, ambient fuel and fuel saturated with water.

FIG. 2 shows a graph depicting the output of detector 30 over time as the probe is moved between fuel samples with different amounts of water dissolved therein. The results in this experiment were obtained for probe in which the grating section was not lapped.

Firstly the dry probe was inserted into dried fuel (i.e. kerosene dried using molecular sieves). After an equilibration period, the Bragg wavelength measured by the detector was about 1564.45 nm. Upon insertion into fuel at ambient conditions (i.e. containing a small amount of water, e.g. 30 ppm), an immediate effect is seen on the Bragg wavelength as water begins to diffuse into the fibre. At equilibrium, the detected Bragg wavelength stabilises at about 1564.65 nm. Similarly, upon insertion into fuel that is saturated with water, there is an immediate increase in the Bragg wavelength. In this case the detected Bragg wavelength at equilibrium stabilised at 1566.35 nm.

To show the reversibility of the detection mechanism, the probe was then inserted back into ambient fuel. An immediate drop in the Bragg wavelength is seen. Similarly, on subsequently inserting the probe into dry fuel, the Bragg wavelength falls again and stabilises at about 1564.45 nm.

REFERENCES

[1] S. D. Puckett, G. E. Pacey: "Detection of water in jet fuel using layer-by-layer thin film coated long period grating sensor". Talanta 78 (2009) 300-304
[2] D. Sáez-Rodriguez, J. L. Cruz Munoz, I. Johnson, D. J. Webb, M. C. J. Large, A. Argyros: "Long period fibre gratings photoinscribed in a microstructured polymer optical fibre by UV radiation". Proc. of SPIE Vol. 7357, 73570L (2009)
[3] T. L. Yeo, T. Sun, K. T. V. Grattan: "Fibre-optic sensor Technologies for humidity and moisture measurement". Sensors and Actuators A 144 (2008) 280-295
[4] S. Muto, O. Suzuki, T. Amano, M. Morisawa: "A plastic optical fibre sensor for real-time humidity monitoring". Meas. Sci. Technol. 14 (2003) 746-750
[5] N. G. Harbach: "Fiber bragg gratings in polymer optical fibers", These EPFL, no 4021 (2008)

The invention claimed is:

1. A water-in-fuel sensor comprising:
   a probe for immersing in liquid fuel, the probe comprising an uncoated polymer optical fibre (POF) for guiding optical radiation, the POF being made of water-permeable plastic material and having a grating section comprising a periodic refractive index modulation that exhibits a characteristic reflection or transmission profile;
   a light source optically coupled to the probe to deliver optical radiation into the POF; and
   a detector arranged to receive optical radiation reflected from or transmitted by the grating section and monitor the characteristic reflection or transmission profile of the grating section,
   wherein the POF permits water dissolved in the liquid fuel to diffuse into the POF at the grating section to cause a water-specific change to the characteristic reflection or transmission profile of the grating section.

2. A water-in-fuel sensor according to claim 1, wherein the grating section comprises a Bragg grating (FBG) or a long period grating (LPG).

3. A water-in-fuel sensor according to claim 1, wherein the light source is arranged to couple broadband optical radiation into the POF, and wherein the detector is arranged to detect a spectrum of optical radiation reflected from or transmitted by the grating section.

4. A water-in-fuel sensor according to claim 1, wherein the light source is arranged to couple optical radiation with a single tuneable frequency into the POF, and wherein the detector is arranged in a feedback loop with the light source to detect a resonant frequency of the grating section.

5. A water-in-fuel sensor according to claim 1, wherein the POF is made of a poly(methyl methacrylate)-based (PMMA-based) material.

6. A water-in-fuel sensor according to claim 1, wherein the amount of water dissolved in the liquid fuel is less than 100 parts per million (ppm).

7. A water-in-fuel sensor according to claim 1, wherein the POF comprises a core made from water-permeable plastic having a first refractive index, and cladding surrounding the core having a second refractive index, the second refractive index being lower than the first refractive index.

8. A water-in-fuel sensor according to claim 7, wherein the cladding has a region of reduced thickness at the grating section.

9. A water-in-fuel sensor according to claim 7, wherein the periodic refractive index modulation is confined within the core.

10. A water-in-fuel sensor according to claim 9, wherein the cladding has a region of reduced thickness at the grating section.

11. A water-in-fuel sensor according to claim 10, wherein the grating section comprises a Bragg grating (FBG) or a long period grating (LPG).

12. A water-in-fuel sensor according to claim 11, wherein the detector is arranged to monitor the resonant wavelength of the FBG or LPG.

13. A water-in-fuel sensor according to claim 11, wherein the light source is arranged to couple broadband optical radiation into the POF, and wherein the detector is arranged to detect a spectrum of optical radiation reflected from or transmitted by the grating section.

14. A water-in-fuel sensor according to claim 11, wherein the light source is arranged to couple optical radiation with a single tuneable frequency into the POF, and wherein the detector is arranged in a feedback loop with the light source to detect a resonant frequency of the grating section.

15. A water-in-fuel sensor according to claim 11, wherein the POF is made of a poly(methyl methacrylate)-based (PMMA-based) material.

16. A water-in-fuel sensor according to claim 15, wherein the POF comprising cladding made of substantially pure PMMA surrounding a core made of PMMA mixed with one or more other polymers to increase its refractive index.

17. A water-in-fuel sensor according to claim 16, wherein the other polymers in the core include one or more photosensitivity enhancing polymers.

18. A method of detecting water in fuel, the method comprising:
   immersing a probe in liquid fuel, the probe comprising a polymer optical fibre (POF) for guiding optical radiation, the POF being made of water-permeable plastic material and having a grating section comprising a periodic refractive index modulation that exhibits a characteristic reflection or transmission profile;
   delivering optical radiation to the probe from a light source optically coupled to the probe;
   receiving optical radiation reflected from or transmitted by the grating section at a detector; and
   monitoring the characteristic reflection or transmission profile of the grating section,
   wherein the POF is uncoated, whereby water dissolved in the liquid fuel diffuses into the POF at the grating section to cause a water-specific change to the characteristic reflection or transmission profile of the grating section.

* * * * *